(12) United States Patent
Kim et al.

(10) Patent No.: US 11,911,508 B2
(45) Date of Patent: Feb. 27, 2024

(54) MICROPARTICLES CONTAINING DUTASTERIDE, AND PREPARATION METHOD THEREFOR

(71) Applicant: INVENTAGE LAB INC., Seongnam-si (KR)

(72) Inventors: Ju Hee Kim, Seongnam-si (KR); Se Yeon Kim, Suwon-Si (KR)

(73) Assignee: INVENTAGE LAB INC., Seongnam-si (KR)

( * ) Notice: Subject to any disclaimer, the term of this patent is extended or adjusted under 35 U.S.C. 154(b) by 607 days.

(21) Appl. No.: 17/056,711

(22) PCT Filed: May 20, 2019

(86) PCT No.: PCT/KR2019/005986
§ 371 (c)(1),
(2) Date: Nov. 18, 2020

(87) PCT Pub. No.: WO2019/225924
PCT Pub. Date: Nov. 28, 2019

(65) Prior Publication Data
US 2021/0205221 A1    Jul. 8, 2021

(30) Foreign Application Priority Data

May 21, 2018  (KR) .................. 10-2018-0057696
May 14, 2019  (KR) .................. 10-2019-0056391

(51) Int. Cl.
*A61K 9/16*    (2006.01)
*A61K 31/58*   (2006.01)
*A61K 47/34*   (2017.01)

(52) U.S. Cl.
CPC .............. *A61K 9/167* (2013.01); *A61K 31/58* (2013.01); *A61K 47/34* (2013.01)

(58) Field of Classification Search
CPC ................................ A61K 9/167; A61K 31/58
See application file for complete search history.

(56) References Cited

U.S. PATENT DOCUMENTS 5,565,467 A    10/1996  Batchelor et al.

FOREIGN PATENT DOCUMENTS

| KR | 101055412 B1 | 8/2011 |
| KR | 20150002446 A | 1/2015 |

(Continued)

OTHER PUBLICATIONS

Xie et al (Controlled Release of Dutasteride from Biodegradable Microapheres In Vitro and In Vivo Studies, PloS one, vol. 9, No. 12, thesis No. 114835, (Year: 2014).*

(Continued)

*Primary Examiner* — Carlos A Azpuru
(74) *Attorney, Agent, or Firm* — STIP Law Group, LLC

(57) ABSTRACT

The present invention relates to: sustained-release microparticles capable of maintaining, for a long time, effects of preventing, treating or alleviating benign prostatic hyperplasia and prostate cancer and effects of preventing hair loss and promoting hair growth according to the administration of microparticles containing dutasteride; and a preparation method therefor, and according to the use of a method for administering the particles to a patient through an injection, a patient does not have to directly store or handle the microparticles, unlike an oral dosage form, and thus storage and handling are simple. In addition, drug effects are maintained for a long period of time of 1-3 months and, simultaneously, administration through injection can be facilitated since foreign body sensation and pain are reduced when being administered to a patient through injection because of the constant average diameter of the particles.

6 Claims, 4 Drawing Sheets

(56) References Cited

FOREIGN PATENT DOCUMENTS

KR    20170009700 A    1/2017
KR    20180009005 A    1/2018

OTHER PUBLICATIONS

Xei et al, Controlled Release of Dutasteride from Biodegradable Microspheres : In Vitro and In Vivo, PloS One, vol. 9, No. 2, pp. 1-23. (Year: 2014).*
Kim et al, Thee Months Extended-Release Microspheres Prepared by Multi-MicroChannel Microfluidics in Beagle Dog Model, International Journal of Pharmaceutics, vol. 608. (Year: 2021).*
International Search Report of PCKR2019/005986, dated Sep. 5, 2019, English translation.
Xiangyang Xie et al, Controlled Release of Dutasteride from Biodegradable Microspheres: In Vitro and In Vivo Studies, PLOS One, Dec. 26, 2014, vol. 9 , No. 12, Thesis No. e114835, pp. 1-23, CrossMark, Lynnfield, USA.

* cited by examiner

MICROPARTICLES CONTAINING DUTASTERIDE, AND PREPARATION METHOD THEREFOR

CROSS-REFERENCE TO RELATED APPLICATIONS

This application is the U.S. National Phase under 35 U.S.C. § 371 of International Application No. PCT/KR2019/005986 filed on May 20, 2019, which in turn claims the benefit of Korean Applications No. 10-2018-0057696 filed on May 21, 2018, and No. 10-2019-0056391 filed on May 14, 2019, the disclosures of which are incorporated by reference into the present application.

TECHNICAL FIELD

The present disclosure relates to microparticles containing dutasteride and a preparation method therefor; more particularly, to microparticles containing dutasteride (a physiologically active substance which can be used in the treatment of prostatic hyperplasia, prostate cancer and alopecia) and a biodegradable polymer, and a preparation method therefor.

BACKGROUND ART

Dutasteride represented by the following Formula 1 (compound: 170-N-(2,5-bis(trifluoromethyl))phenylcarbamoyl-4-aza-5α-androst-1-en-3-one), a dual 5-alpha reductase inhibitor that inhibits both type 1 and type 2 5-alpha reductase, is known to be useful in the treatment of benign prostatic hyperplasia, prostate cancer and male pattern alopecia by inhibiting the conversion of testosterone to dihydrotestosterone (DHT).

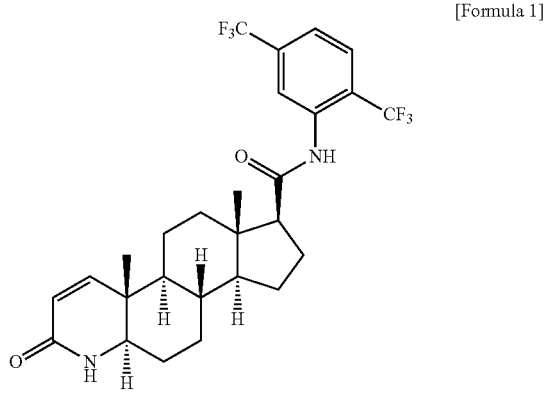

[Formula 1]

Dutasteride is currently marked under the product name AVODART®, where AVODART® is a product made by dissolving 0.5 mg of dutasteride in 349.5 mg of a mixture of caprylic/capric mono- and di-glyceride oils and butylated hydroxytoluene (BHT) then filling a soft capsule with the resulting mixture.

However, one of the disadvantages of AVODART® is its inconvenience of administration due to the relatively large amount of excipient compared to the amount of active ingredient, which makes the volume of the soft capsule large.

Conventionally, a study on a method of decreasing the volume of oral formulations containing dutasteride has been conducted to increase both the convenience of taking the oral formulation and the stability of elution.

That is, as in the prior art, there has been an attempt to decrease the volume of the oral formulation to increase the convenience of taking the oral formulation, but no study on sustained-release formulations capable of maintaining efficacy for a long period of time has been conducted in consideration of the fact that the oral formulation needs to be taken every day.

Thus, there is an urgent need to develop a therapeutic agent for prostatic hyperplasia, prostate cancer and alopecia that can: solve the problems of the conventional formulation containing dutasteride; maintain the efficacy thereof for 1 month or more with a single administration; and be simple to store and handle.

PRIOR ART DOCUMENTS

Patent Documents (Patent Document 1) U.S. Pat. No. 5,565,467 A
(Patent Document 2) KR 10-1833280 B1

DISCLOSURE

Technical Problem

The present disclosure relates to microparticles containing dutasteride and a preparation method therefor.

An object of the present disclosure is to provide sustained-release microparticles, capable of maintaining, for 1 to 3 months, effects of preventing, treating or alleviating prostatic hyperplasia and prostate cancer and effects of preventing hair loss and promoting hair growth when said microparticles containing dutasteride are administered, unlike an oral formulation that has to be taken daily, and a preparation method therefor.

Another object of the present disclosure is to provide microparticles containing dutasteride capable of being easily stored and handled, by being administered to a patient through an injection and removing the of patients to directly store or handle the microparticles containing dutasteride, unlike an oral formulation.

Still another object of the present disclosure is to provide sustained-release microparticles containing dutasteride capable of maintaining a drug administration effect for a long period of time of 1 to 3 months, constantly maintaining an effective concentration of the drug by being prepared as microparticles having a constantly micro-sized average diameter and controlling release of the drug from the microparticles, and reducing foreign body sensation and pain when applied to an injectable agent composed of particles having a uniform size and administered to a patient as the injectable agent.

Technical Solution

As an embodiment of the present disclosure, the present disclosure relates to dutasteride-containing microparticles, comprising dutasteride and a biodegradable polymer, wherein the microparticles have a dutasteride drug evenly distributed in spherical biodegradable polymer microparticles, and has an average particle diameter of 20 to 70 μm.

As an embodiment of the present disclosure, the microparticles of the present disclosure may contain the biodegradable polymer and dutasteride at a weight ratio of 3:1 to 9:1.

As an embodiment of the present disclosure, the microparticles of the present disclosure may continuously release dutasteride for 1 to 3 months.

As an embodiment of the present disclosure, the biodegradable polymer of the present disclosure may be selected from the group consisting of, but is not limited to, polylactic acid, polylactide, polylactic-co-glycolic acid, polylactide-co-glycolide (PLGA), polyphosphazine, polyiminocarbonate, polyphosphoester, polyanhydride, polyorthoester, polycaprolactone, polyhydroxyvalate, polyhydroxybutyrate, polyamino acid, and a combination thereof, preferably polylactide-co-glycolide (PLGA).

As an embodiment of the present disclosure, the microparticles of the present disclosure may be prepared by using microchannels, and a ratio of a width (w) of a cross section in the microchannel to an average diameter (d') of the microparticles may be in the range of 0.7 to 1.3.

As an embodiment of the present disclosure, the microparticles of the present disclosure may be prepared by using the microchannels, and a ratio of a depth (d) of a cross section in the microchannel to the average diameter (d') of the microparticles may be in the range of 0.7 to 1.3.

As an embodiment of the present disclosure, a composition for treating and preventing hair loss and promoting hair growth according to the present disclosure may comprise the microparticles as described above.

As an embodiment of the present disclosure, a composition for preventing, treating or alleviating prostatic hyperplasia and prostate cancer according to the present disclosure may comprise the microparticles as described above.

As an embodiment of the present disclosure, the present disclosure relates to a method of preparing dutasteride-containing microparticles, comprising steps of: 1) preparing a first mixture by dissolving a biodegradable polymer and dutasteride in an organic solvent; 2) preparing a second mixture by dissolving a surfactant in water; 3) injecting the first mixture of the step 1) into a microchannel in a linear direction and allowing the first mixture to flow therein; 4) preparing microparticles having dutasteride evenly distributed in spherical biodegradable polymer particles by injecting the second mixture of the step 2) into a microchannel formed on either side or one side so as to form a cross-point with the microchannel in which the first mixture of the step 3) flows in the linear direction and allowing the second mixture to flow therein, and then crossing the flow of the first mixture in the linear direction with the flow of the second mixture; 5) collecting the microparticles generated at the cross-point of the step 4); 6) evaporating and removing the organic solvent present in the microparticles by stirring the microparticles collected in the step 5); and 7) washing and drying the microparticles of the step 6), wherein the microparticles have an average particle diameter of 20 to 70 μm.

As an embodiment of the present disclosure, the first mixture of the step 1) of the present disclosure may contain 10 to 20% by weight of a biodegradable polymer.

As an embodiment of the present disclosure, the first mixture of the step 1) of the present disclosure may contain a biodegradable polymer and dutasteride at a weight ratio of 3:1 to 9:1.

As an embodiment of the present disclosure, the biodegradable polymer of the present disclosure may be selected from the group consisting of, but is not limited to, polylactic acid, polylactide, polylactic-co-glycolic acid, polylactide-co-glycolide (PLGA), polyphosphazine, polyiminocarbonate, polyphosphoester, polyanhydride, polyorthoester, polycaprolactone, polyhydroxyvalate, polyhydroxybutyrate, polyamino acid, and a combination thereof, preferably polylactide-co-glycolide (PLGA).

As an embodiment of the present disclosure, the organic solvent of the step 1) of the present disclosure may be one or more selected from the group consisting of dichloromethane, chloroform, chloroethane, dichloroethane, trichloroethane, and a mixture thereof.

As an embodiment of the present disclosure, the second mixture of the step 2) of the present disclosure may contain 0.2% to 0.3% by weight of a surfactant.

As an embodiment of the present disclosure, the surfactant of the step 2) of the present disclosure may be one or more selected from the group consisting of nonionic surfactants, anionic surfactants, cationic surfactants, and a mixture thereof.

As an embodiment of the present disclosure, in the step 3) of the present disclosure, the first mixture may be injected into the microchannel in the linear direction at a pressure of 600 to 1,000 mbar.

As an embodiment of the present disclosure, in the step 4) of the present disclosure, the second mixture may be injected into the microchannel formed on either side or one side so as to form the cross-point with the microchannel in the linear direction in which the first mixture flows, and the second mixture may be injected at a pressure of 1,200 to 1,600 mbar.

As an embodiment of the present disclosure, in the step 5) of the present disclosure, the microparticles may be collected in a water bath containing a mixed solution containing 0.2% to 0.3% by weight of a surfactant.

As an embodiment of the present disclosure, the step 6) of the present disclosure may include steps of: 6-1) performing a first stirring on the microparticles at a speed of 800 to 1,200 rpm for 1 to 2 hours at 14 to 16° C.; 6-2) after the first stirring, performing a second stirring on the microparticles subjected to the first stirring at a speed of 800 to 1,200 rpm for 0.5 to 1.5 hours at 19 to 21° C.; and 6-3) after the second stirring, performing a third stirring on the microparticles subjected to the second stirring at a speed of 800 to 1,200 rpm for 0.5 to 1.5 hours at 24 to 26° C.

As an embodiment of the present disclosure, the microchannels of the step 3) and step 4) of the present disclosure may be formed on a surface of a wafer, and may have an average diameter of 40 to 100 μm, preferably 40 to 60 μm, and more preferably 50 μm, but the average diameter thereof is not limited thereto.

Advantageous Effects

The present disclosure relates to microparticles containing dutasteride and a preparation method therefor, and more particularly, to sustained-release microparticles capable of maintaining, for 1 to 3 months, effects of preventing, treating or alleviating prostatic hyperplasia and prostate cancer and effects of preventing hair loss and promoting hair growth when the microparticles containing dutasteride are administered, and a preparation method therefor.

In addition, the present disclosure is used according to a method of administering the microparticles containing dutasteride to a patient through an injection. Thus, the patient does not have to directly store or handle the microparticles, unlike an oral formulation, and thus storage and handling may be simple. Further, drug effects may be maintained for a long period of time of 1 to 3 months, and the microparticles are prepared as microparticles having a constantly micro-sized average diameter. Thus, the microparticles may reduce foreign body sensation and pain when being administered to a patient as injectable agent, and thus facilitate administration as an injectable agent.

BEST MODE

The present disclosure relates to dutasteride-containing microparticles, comprising dutasteride and a biodegradable polymer, wherein the microparticles have a dutasteride drug evenly distributed in a spherical biodegradable polymer, and has an average particle diameter of 20 to 70 μm.

Hereinafter, embodiments of the present disclosure will be described in detail so as to be easily carried out by a person skilled in the art to which the present disclosure pertains. However, the present disclosure may be implemented in various different forms and is not limited to embodiments described herein.

Figure 1:
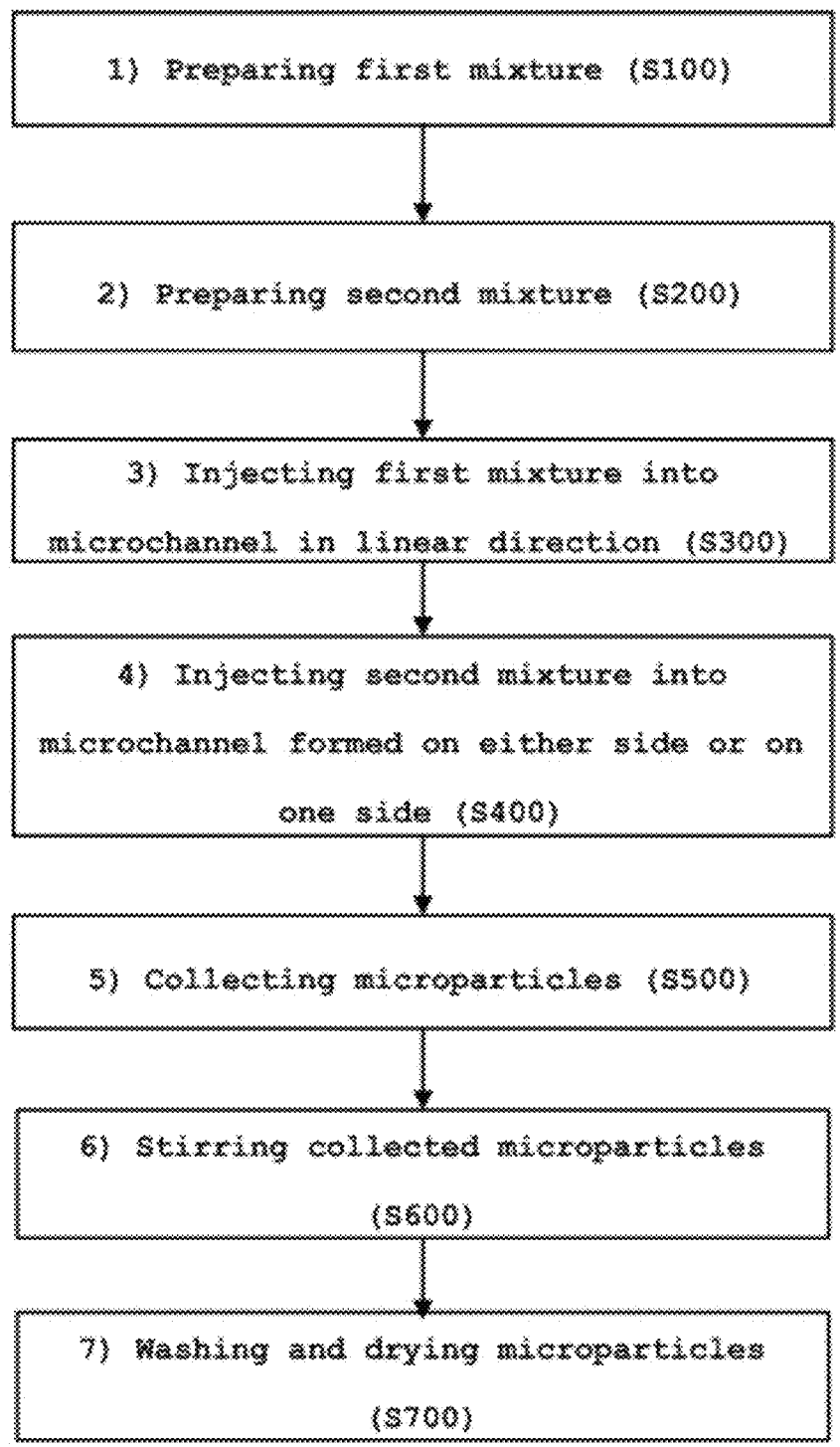
FIG. 1 is a flow chart for a preparation method of microparticles containing dutasteride according to the present disclosure.

FIG. 1 is a flow chart for a preparation method of microparticles containing dutasteride according to the present disclosure.

According to the flow chart, the microparticles containing dutasteride according to the present disclosure are prepared in the order of preparing a first mixture (S100); preparing a second mixture (S200); injecting the first mixture into a microchannel in a linear direction (S300); injecting the second mixture into a microchannel formed on either side or on one side (S400); collecting the microparticles (S500); stirring the collected microparticles (S600); and washing and drying the microparticles (S700).

More specifically, a method of preparing microparticles containing dutasteride according to an embodiment of the present disclosure will be described as follows.

The step S100, which is a step of preparing a first mixture, is a step of preparing a first mixture by dissolving a biodegradable polymer and dutasteride in an organic solvent, and the biodegradable polymer is selected from the group consisting of, but is not limited to, polylactic acid, polylactide, polylactic-co-glycolic acid, polylactide-co-glycolide (PLGA), polyphosphazine, polyiminocarbonate, polyphosphoester, polyanhydride, polyorthoester, polycaprolactone, polyhydroxyvalate, polyhydroxybutyrate, polyamino acid, and a combination thereof, preferably polylactide-co-glycolide (PLG).

In addition, the organic solvent is water immiscible and is, but is not limited to, for example, one or more selected from the group consisting of chloroform, chloroethane, dichloroethane, trichloroethane, and a mixture thereof, preferably dichloromethane. The organic solvent is an organic solvent capable of dissolving the biodegradable polymer and dutasteride and is not limited thereto, and any organic solvent can be used as long as it can be easily selected by those skilled in the art.

The step S100 is a step of preparing a first mixture in which a biodegradable polymer and dutasteride are dissolved, and as a solvent, the organic solvent described above is used. In the above step, the biodegradable polymer and dutasteride are completely dissolved by using the organic solvent using dissolution properties of the dutasteride and the biodegradable polymer. After biodegradable polymer and dutasteride are completely dissolved, the first mixture contains the biodegradable polymer and dutasteride at a weight ratio of 3:1 to 9:1, and preferably 4:1, but the weight ratio is not limited thereto. If the weight ratio of the biodegradable polymer and dutasteride is less than 3:1, that is, if the biodegradable polymer is included less than the weight ratio above, the weight ratio of the biodegradable polymer is smaller than that of the dutasteride, such that it may be difficult to prepare the microparticles containing the dutasteride evenly distributed in the spherical biodegradable polymer particle. If the weight ratio of the biodegradable polymer and dutasteride exceeds 9:1, that is, if the biodegradable polymer is contained in excess of the weight ratio above, the content of the dutasteride in the microparticles is small, such that it may be necessary to administer a large amount of microparticles in order to administer a desired concentration of drug.

More specifically, the biodegradable polymer in the first mixture is contained in an amount of 10 to 20% by weight, preferably 15% by weight, but the amount is not limited thereto.

In the step S200, which is a step of preparing a second mixture, the second mixture is prepared by dissolving a surfactant in water. As the surfactant, any surfactant may be used without limitation as long as the surfactant can help the biodegradable polymer solution form a stable emulsion. Specifically, the surfactant is one or more selected from the group consisting of nonionic surfactants, anionic surfactants, cationic surfactants, and a mixture thereof, and more specifically, one or more selected from the group consisting of methylcellulose, polyvinylpyrrolidone, lecithin, gelatin, polyvinyl alcohol, polyoxyethylene sorbitan fatty acid ester, polyoxyethylene castor oil derivative, sodium lauryl sulfate, sodium stearate, ester amine, linear diamine, fatty amine, and a mixture thereof, preferably polyvinyl alcohol, and is not limited thereto.

The step S300 and step S400 are steps of injecting the first mixture and the second mixture into microchannels formed on a wafer and allowing the first mixture and the second mixture to flow therein.

More specifically, aluminum is deposited on a silicon wafer using an e-beam evaporator, and a photoresist is patterned on the aluminum using a photolithography technique. Thereafter, aluminum is etched using the photoresist as a mask, the photoresist is removed, silicon is etched with deep ion reactive etching (DRIE) using aluminum as a mask, and then, glass is anodic bonded onto the wafer to be sealed after the aluminum is removed, thereby preparing the microchannel.

In addition, the microchannel has, but is not limited to, an average diameter of 40 to 100 μm, preferably 40 to 60 μm, and more preferably 50 µm. If the microchannel has an average diameter of 40 µm or less, there is a possibility that the microparticles will be prepared as small microparticles having a diameter of 20 µm or less, so the microparticles are highly likely to being engulfed by macrophages after injection into the human body, thereby affecting the release of effective drugs and the absorption thereof in vivo. In addition, if the microchannel has an average diameter of 100 µm or more, there is a possibility that the prepared microparticles will have a diameter of 70 µm or more, so foreign body sensation and pain may be increased when the injectable agent is administered, and the particle size distribution of the prepared particles may be increased, thereby making it difficult to prepare microparticles having a uniform particle size.

Figure 6:
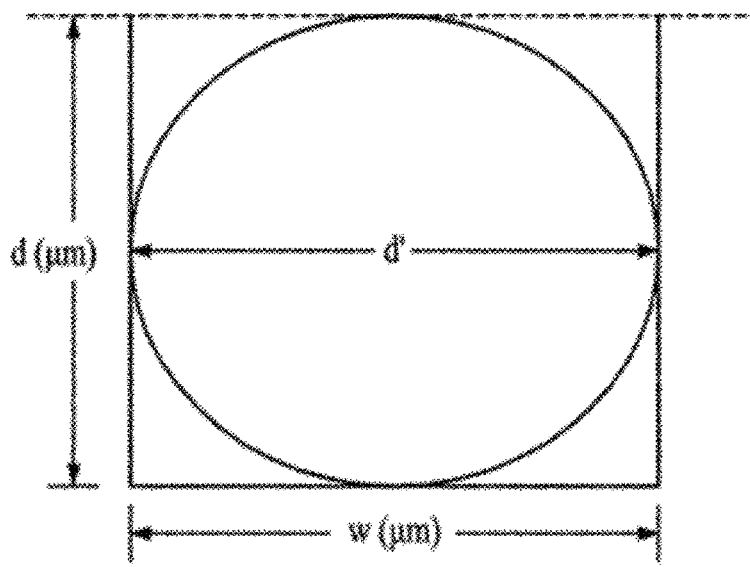
FIG. 6 is a diagram illustrating a relationship between an average diameter of the microparticles and a cross section of the microchannel.

In addition, the width (w) and the depth (d) of a cross section in the microchannel are closely related to an average diameter (d') of the microparticles to be prepared. As shown in FIG. 6, the width (w) of the cross section in the microchannel is in the range of 0.7 to 1.3 ratio relative to the average diameter (d') of the microparticles, and the ratio of the depth (d) of the cross section in the microchannel to the average diameter (d') of the microparticles is in the range of 0.7 to 1.3.

That is, once the average diameter (d') of the microparticles to be prepared is determined, it is possible to prepare microparticles having a desired size only when a ratio of the width (w) and depth (d) of the cross section in the microchannel to the d' are set in the range of 0.7 to 1.3.

The step S300 is a step of injecting the first mixture into a microchannel in a linear direction and allowing the first mixture to flow therein. The step S400 is a step of injecting the second mixture into a microchannel formed on either side or one side so as to form a cross-point with the microchannel in the linear direction and allowing the second mixture to flow therein.

That is, the first mixture flows along the microchannel in the linear direction, and the second mixture flows along the microchannel forming the cross-point with the microchannel in the linear direction on either side or one side with respect to the microchannel in the linear direction and meets the flow of the first mixture.

At this time, when injected into the microchannel in a linear direction, the first mixture is injected under a constant pressure condition and allowed to flow at a constant flow rate, and at this time, the pressure condition is 600 to 1,000 mbar, preferably 800 mbar, but is not limited thereto. In addition, when injected into the microchannel in either side or one side, the second mixture is injected under a constant pressure condition and allowed to flow at a constant flow rate, and at this time, the pressure condition is 1,200 to 1,600 mbar, preferably 1,400 mbar, but is not limited thereto.

That is, in order to make the flow of the second mixture forming a cross-point with the flow of the first mixture faster than the first mixture injected into the microchannel in the linear direction, the second mixture is allowed to flow under a higher pressure condition.

As described above, by varying the flow rates of the first mixture and the second mixture, and making the flow rate of the second mixture faster than that of the first mixture, the second mixture having a relatively faster flow rate compresses the first mixture at the point where the flow of the first mixture meets the flow of the second mixture, and at this time, due to the repulsive force of the first mixture and the second mixture, the biodegradable polymer and dutasteride in the first mixture generate spherical microparticles, and more specifically, microparticles are formed in which the dutasteride is evenly distributed in the spherical biodegradable polymer.

In the step S500, which is a step of collecting the microparticles, the microparticles are collected in the water bath containing the second mixture, thereby preventing aggregation between the initially generated microparticles.

In the step S500, which is a step of using the second mixture prepared in the step S200, that is, a mixed solution of a surfactant and water, after the second mixture is prepared in the step S200, a part thereof is injected into the microchannel, and the other part thereof is moved to the water bath of the step S500, and is used to prevent aggregation between the collected microparticles.

In the step S600, which is a step of stirring the microparticles collected in the water bath, the microparticles are stirred under a constant temperature condition and at a stirring speed to evaporate and remove the organic solvent present on the surfaces of the microparticles. At this time, the step of stirring the microparticles is performed in the order of: a first stirring step under the stirring conditions of a speed of 800 to 1,200 rpm for 1 to 2 hours at 14 to 16° C.; after the first stirring step, a second stirring step under the stirring conditions of a speed of 800 to 1,200 rpm for 0.5 to 1.5 hours at 19 to 21° C.; and after the second stirring step, a third stirring step under the stirring conditions of a speed of 800 to 1,200 rpm for 0.5 to 1.5 hours at 24 to 26° C. The stirring speed is 800 to 1,200 rpm, preferably 1,000 rpm, but is not limited thereto. The stirring speed for stirring the microparticles is the same for all of the first, second and third stirring, but the stirring is characterized by being performed while the stirring temperature is gradually increased. As the stirring temperature is increased stepwise, the evaporation rate of the organic solvent present on the surface of the microparticles may be adjusted. That is, by gradually evaporating the organic solvent present on the surface of the microparticles, it is possible to prepare the microparticles with a smooth surface.

More specifically, in the step S600, the first stirring step is performed at 14 to 16° C. for 1 to 2 hours, and preferably at 15° C. for 1.5 hours. Thereafter, the second stirring step is performed at 19 to 21° C. for 0.5 to 1.5 hours, and preferably at 20° C. for 1 hour. Thereafter, the third stirring step is performed at 24 to 26° C. for 0.5 to 1.5 hours, and preferably at 25° C. for 1 hour.

The temperature at which the first mixture and the second mixture flow through the microchannels is also 14 to 16° C., preferably 15° C. That is, after flowing through the microchannel and forming the cross-point to generate microparticles, the first mixture and the second mixture are kept at a constant low temperature of 14 to 16° C. until the collected microparticles are subjected to the first stirring step. It is possible to prepare and maintain spherical particles only when a low temperature is maintained during the preparing process of the microparticles. That is, in the case of non-low temperature conditions, it is difficult to prepare a constantly spherical particle.

Finally, in the step S700, which is a step of washing and drying the microparticles, the microparticles from which all the organic solvents on the surface thereof are removed by stirring are washed several times with purified water filtered through sterilization to remove the surfactant remaining on the microparticles, and then freeze-dried.

The finally produced microparticles have dutasteride drugs evenly distributed in the spherical biodegradable polymer microparticles, and the microparticles have an average particle diameter of 20 to 70 µm and contain the biodegradable polymer and dutasteride at a weight ratio of 3:1 to 9:1. If the average particle diameter of the microparticles is less than 20 μm, the microparticles are highly likely to being engulfed by macrophages after injection into the human body, thereby affecting the release of the drug from the particles and the absorption thereof in vivo. If the average particle diameter of the microparticles exceeds 70 μm, a thick gauge syringe needle is used to a patient to which the injectable agent containing the microparticles is administered, thereby increasing pain during drug administration.

The weight ratio of the biodegradable polymer and dutasteride contained in the microparticles is the same as that in the first mixture. Thus, microparticles containing the biodegradable polymer and dutasteride may be prepared at the same ratio as the weight ratio in the first mixture by preparing the microparticles and evaporating and removing all organic solvents.

Example 1

Preparation of Microparticles Containing Dutasteride

A first mixture was prepared by dissolving polylactide-co-glycolide (PLGA) and dutasteride in dichloromethane. At this time, the polylactide-co-glycolide in the first mixture is contained in an amount of 15% by weight, and the weight ratio of polylactide-co-glycolide and dutasteride is 4:1.

Polyvinyl alcohol as a surfactant was mixed with water to prepare a second mixture containing 0.25% by weight of polyvinyl alcohol.

The first mixture and the second mixture were injected into a microchannel formed on a silicon wafer and allowed to flow therein. At this time, in order for the first mixture and the second mixture to flow at a constant flow rate, the first mixture was allowed to flow under a pressure condition of 800 mbar and the second mixture was allowed to flow under a pressure condition of 1,400 mbar. The temperature condition was maintained at 15° C.

Microparticles generated at the cross-point where the flow of the first mixture meets the flow of the second mixture were collected in a water bath containing the second mixture. The microparticles collected in the water bath were firstly stirred at 15° C. for 1.5 hours at a speed of 1,000 rpm, and then was secondly stirred for 1 hour at a speed of 1,000 rpm with the temperature raised to 20° C., and was thirdly stirred at a speed of 1,000 rpm for 1 hour with the temperature raised to 25° C.

After the stirring was completed, the microparticles were washed several times with purified water, filtered through sterilization, and freeze-dried to prepare final microparticles.

Example 2

Example 2 was performed in the same manner as in Example 1, except that the weight ratio of polylactide-co-glycolide and dutasteride was 9:1.

Example 3

Example 3 was performed in the same manner as in Example 1, except that the weight ratio of polylactide-co-glycolide and dutasteride was 2:1.

Example 4

Example 4 was performed in the same manner as in Example 1, except that the weight ratio of polylactide-co-glycolide and dutasteride was 12:1.

Examples 5 to 9

Examples 5 to 9 were performed in the same manner as in Example 1, but the microparticles were collected in a water bath containing the second mixture, and then the stirring process was performed under the conditions shown in Table 1 below.

TABLE 1

| | Stirring conditions | Stirring temperature | Stirring time | Stirring speed |
|---|---|---|---|---|
| Example 5 | 1 | 15° C. | 1.5 hours | 800 rpm |
| | 2 | | 1 hour | 1,000 rpm |
| | 3 | | 1 hour | 1,200 rpm |
| Example 6 | 1 | 20° C. | 1.5 hours | 800 rpm |
| | 2 | | 1 hour | 1,000 rpm |
| | 3 | | 1 hour | 1,200 rpm |
| Example 7 | 1 | 25° C. | 1.5 hours | 800 rpm |
| | 2 | | 1 hour | 1,000 rpm |
| | 3 | | 1 hour | 1,200 rpm |
| Example 8 | 1 | 15° C. | 1.5 hours | 800 rpm |
| | 2 | 20° C. | 1 hour | |
| | 3 | 25° C. | 1 hour | |
| Example 9 | 1 | 15° C. | 1.5 hours | 1,200 rpm |
| | 2 | 20° C. | 1 hour | |
| | 3 | 25° C. | 1 hour | |

Experimental Example 1: Examination of Shape of Miroparticles

In order to examine the shape of the microparticles depending on the stirring condition, the shape of the microparticles prepared under the conditions of Example 1 and Examples 5 to 9 was examined through SEM photographs.

The results thereof are shown in Table 2 below.

TABLE 2

| Experiment depending on stirring conditions | Result of preparation of microparticles |
|---|---|
| Example 5 | Δ |
| Example 6 | Δ |
| Example 7 | Δ |
| Example 8 | ○ |
| Example 9 | ○ |
| Example 1 | ○ |

Figure 2:
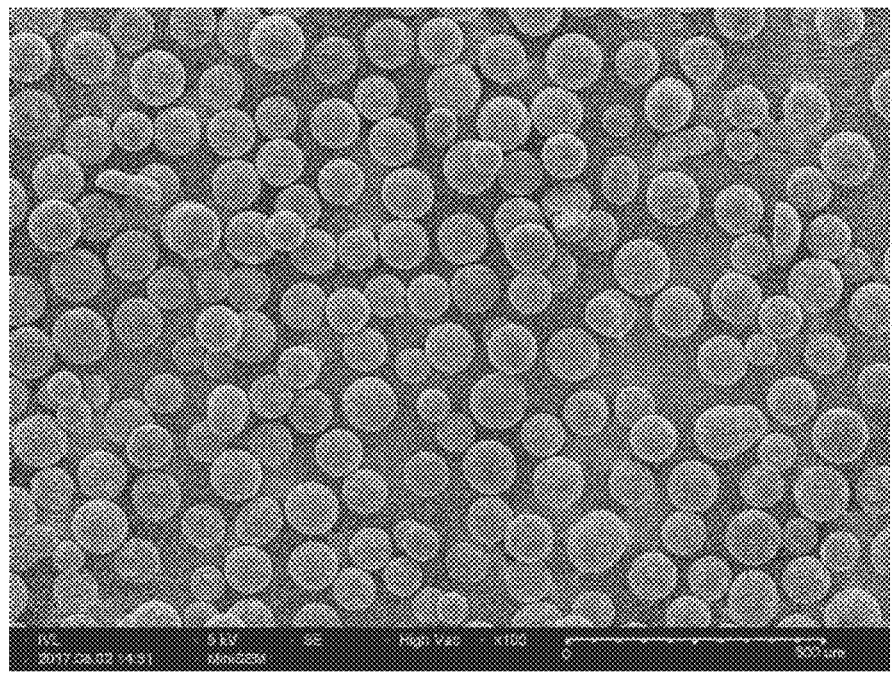
FIG. 2 is an SEM photograph of the microparticles obtained by the preparation method according to an embodiment of the present disclosure.
Figure 3:
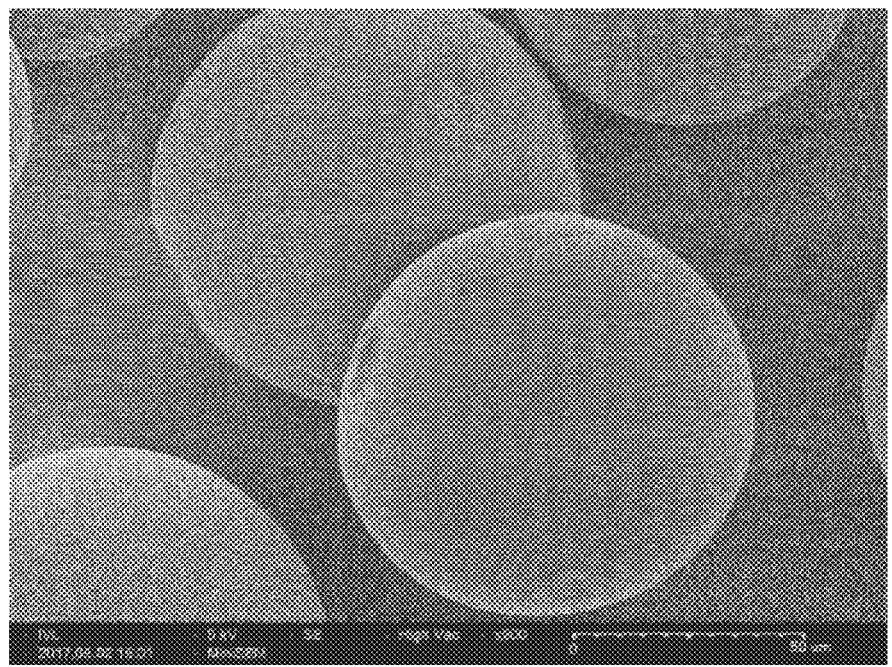
FIG. 3 is an SEM photograph of the microparticles obtained by the preparation method according to an embodiment of the present disclosure.
Figure 4:
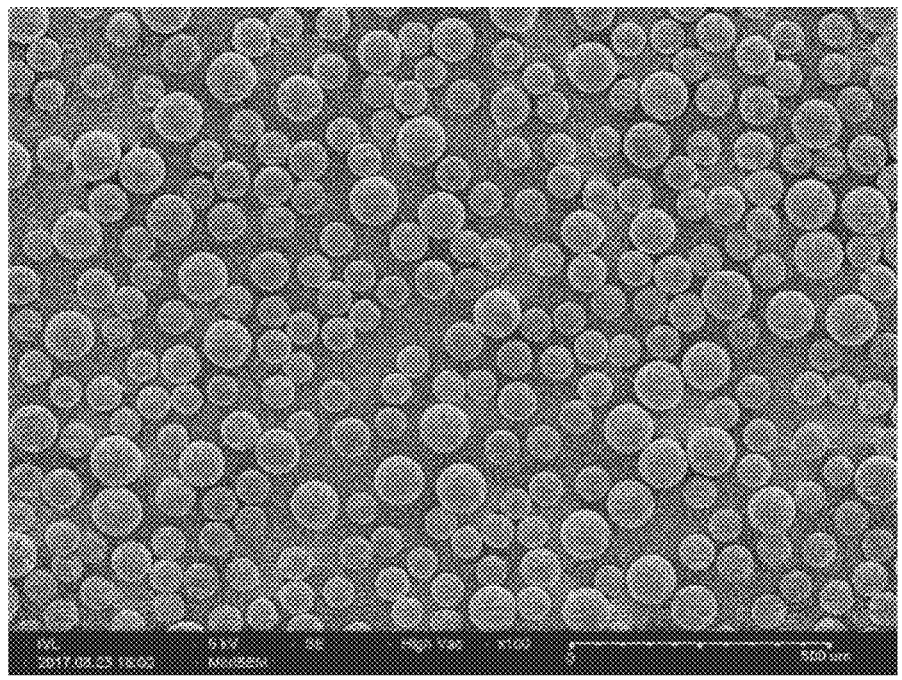
FIG. 4 is an SEM photograph of the microparticles obtained by the preparation method according to an embodiment of the present disclosure.
Figure 5:
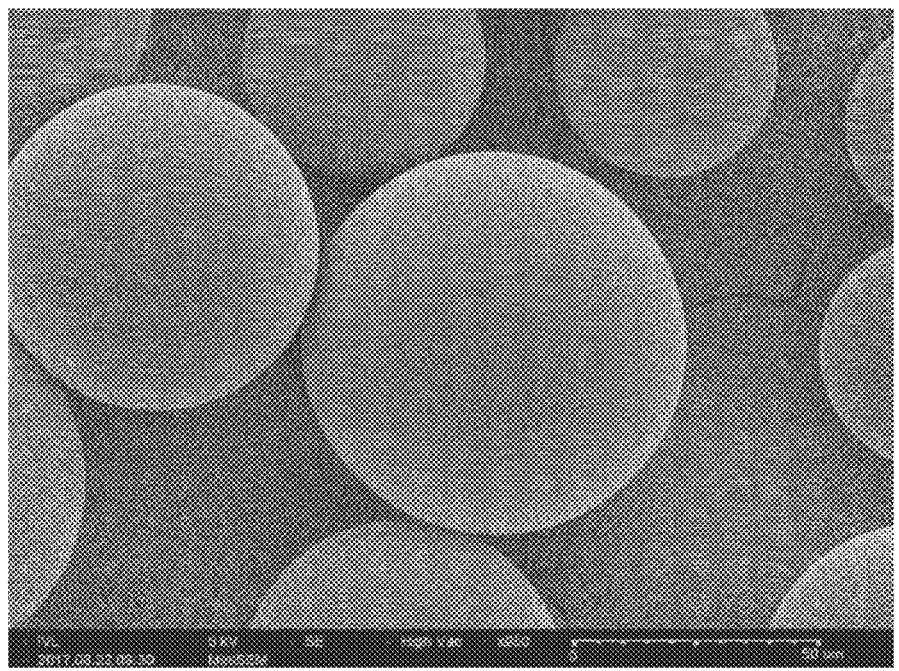
FIG. 5 is an SEM photograph of the microparticles obtained by the preparation method according to an embodiment of the present disclosure.

Δ means that the microparticles were aggregated due to the influence of a residual solvent, and had a un-uniform shape, as shown in the SEM photographs of FIGS. 2 and 3. On the other hand, it was confirmed from Example 1, 8 and 9 that the microparticles had a uniform shape and were not aggregated, as shown in the SEM photographs of FIGS. 4 and 5.

That is, it was confirmed that the temperature conditions affected the shape of the microparticles and the occurrence of aggregation upon stirring.

Experimental Example 2: Evaluation of Degree of Drug Release

The degree of drug release for the microparticles containing dutasteride was evaluated. Whether the microparticles can be used as a long-acting formulation was confirmed by evaluating a release pattern of dutasteride over time.

Experiments were conducted on the microparticles of Examples 1 to 4. As an eluate, a 2% aqueous sodium lauryl sulfate (SLS) solution was used.

More specifically, a 120 mL glass vial was filled with the microparticles equivalent to 10 mg as dutasteride, and 100 mL of the eluate was added thereto, and the vial was closed with a rubber stopper and sealed with an aluminum lid (n=3). The sealed vial was placed in a constant temperature stirring water bath and an elution test was performed for 35 days under conditions of 37° C. and 120 RPM.

Sampling time was set at 0, 1 hr, 2 hr, 4 hr, day 1, day 2, day 4, day 7, day 14, day 21, day 28 and day 35. After sampling 1 mL at each time, 1 mL of a co-elute was supplemented.

The sampled eluted samples were analyzed for the content of dutasteride using HPLC, and each elution rate was calculated.

Figure 7:
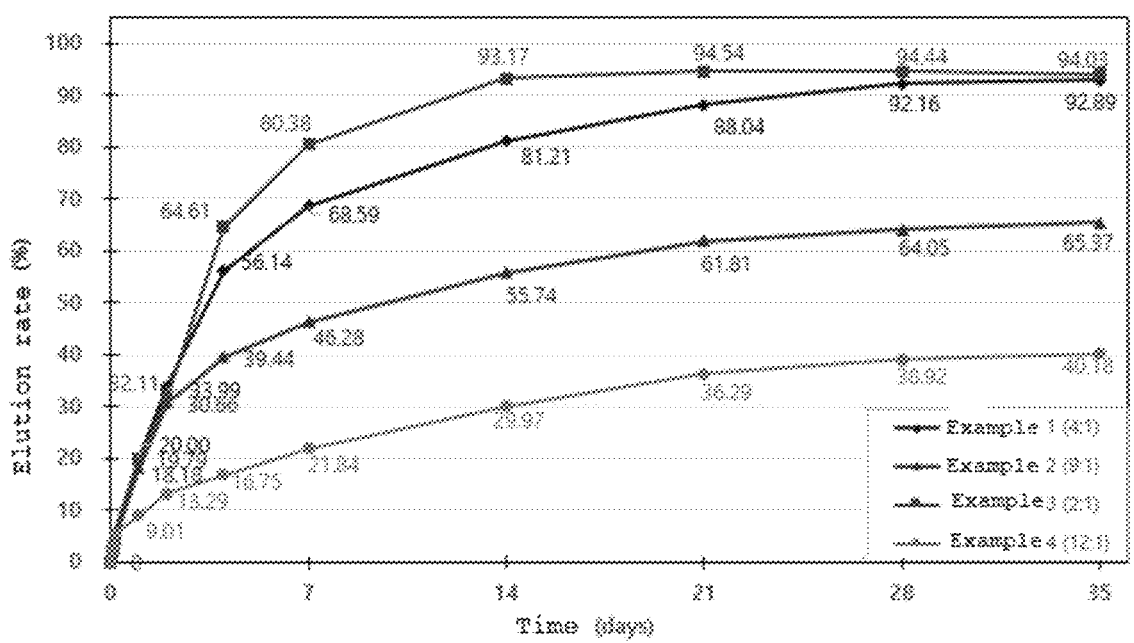
FIG. 7 is an experimental result of a drug release effect depending on the content range of a biodegradable polymer and dutasteride according to an embodiment of the present disclosure.

The experimental results are shown in FIG. 7.

According to the experimental results, the microparticles in Example 1 (4:1) were continuously eluted, 90% or more of which were eluted on day 28. The microparticles in Example 2 (9:1) were eluted less than 70% even on day 28 and day 35. The microparticles in Example 3 (2:1) were eluted 90% or more on day 14, and the elution rate did not increase after day 21. The microparticles in Example 4 (12:1) were eluted at less than 50% even on day 28 and day 35.

According to the above experimental results, the drug release effect is sustained for a long time in the weight ratio range of the biodegradable polymer and dutasteride of the present disclosure, thereby increasing the possibility of application as a sustained-release formulation. On the other hand, if the content range of the biodegradable polymer and dutasteride is less than or exceeds that of the present disclosure, either an initially released amount is very large, a long-acting effect is insufficient (Example 3), or a long-term release effect is excellent but the initially released amount is small, so that the efficacy due to an initial drug release may not be maintained (Example 4).

Preparation Example: Preparation of Composition for Subcutaneous Injection

The microparticles prepared in Example 1 were added to 2.0 ml of a suspension solvent based on one-month aliquot corresponding to API 26 μg/day, and then uniformly suspended to prepare a composition for subcutaneous injection.

The suspension solvent was composed of the composition shown in Table 3 below.

TABLE 3

| Criteria of content | Purpose of mixing | Ingredient name | Amount | Unit |
|---|---|---|---|---|
| 2.0 mL | Isotonic agent | D-Mannitol | 100.0 | mg |
|  | Suspending agent | Sodium carboxymethylcellulose | 10.0 | mg |
|  | Suspending agent | Polysorbate 80 | 10.0 | mg |
|  | Solvent | Injection water | Remainder |  |

Based on Table 3, the microparticles are uniformly contained in the suspension solvent, the microparticles themselves are administered when provided by subcutaneous injection, and dutasteride is released by decomposition of the biodegradable polymer in the body, making it possible to use the microparticles as a sustained-release formulation. Although the preferred embodiments of the present disclosure have been described in detail above, the scope of the present disclosure is not limited thereto, and various modifications and improvements made by those skilled in the art using the basic concept of the present disclosure defined in the following claims also belong to the scope of rights of the present disclosure.

INDUSTRIAL APPLICABILITY

The present disclosure relates to microparticles containing dutasteride and a preparation method therefor, more particularly, to microparticles containing dutasteride (a physiologically active substance which can be used in the treatment of prostatic hyperplasia, prostate cancer and alopecia), and a biodegradable polymer, and a preparation method therefor.

The invention claimed is:

1. Dutasteride-containing microparticles, comprising dutasteride and a biodegradable polymer, wherein,
the microparticles have a dutasteride drug evenly distributed in a spherical biodegradable polymer,
the microparticles have an average particle diameter of 20 to 70 μm,
the microparticles contain the biodegradable polymer and dutasteride at a weight ratio of 3:1 to 9:1,
the microparticles are capable of preventing an initial excessive release of dutasteride after injection into a body, and
the microparticles are capable of maintaining a drug administration effect of dutasteride according to an initial release after injection into the body.

2. The microparticles of claim 1, wherein the microparticles continuously release dutasteride for 1 to 3 months.

3. The microparticles of claim 1, wherein the biodegradable polymer is selected from the group consisting of polylactic acid, polylactide, polylactic-co-glycolic acid, polylactide-co-glycolide (PLGA), polyphosphazine, polyiminocarbonate, polyphosphoester, polyanhydride, polyorthoester, polycaprolactone, polyhydroxyvalate, polyhydroxybutyrate, polyamino acid, and a combination thereof.

4. The microparticles of claim 3, wherein the biodegradable polymer is polylactide-co-glycolide (PLGA).

5. A composition for treating and preventing hair loss and promoting hair growth, comprising the microparticles of claim 1.

6. A composition for preventing, treating or alleviating prostatic hyperplasia and prostate cancer, comprising the microparticles of claim 1.

* * * * *